United States Patent [19]

Fabian

[11] Patent Number: 5,166,967
[45] Date of Patent: Nov. 24, 1992

[54] MARKERS FOR DENTAL X-RAY FILM AND PACKETS FOR SIMPLIFIED FILM MOUNTING

[76] Inventor: Carl E. Fabian, 577 NE. 96th St., Miami Shores, Fla. 33138

[21] Appl. No.: 665,096

[22] Filed: Mar. 6, 1991

Related U.S. Application Data

[63] Continuation-in-part of Ser. No. 572,264, Aug. 27, 1990, abandoned.

[51] Int. Cl.$^5$ .............................................. G03B 42/02
[52] U.S. Cl. ........................................ 378/168; 378/163
[58] Field of Search .............. 378/168, 167, 163, 169, 378/182, 165; 40/159.2

[56] References Cited

U.S. PATENT DOCUMENTS

| 1,748,490 | 2/1930 | Martin | 378/169 |
|---|---|---|---|
| 2,103,961 | 3/1935 | Wilmanns | 378/188 |
| 3,152,252 | 10/1964 | Wainwright et al. | 378/169 |
| 3,851,178 | 11/1974 | Borden | 378/168 |
| 3,936,643 | 2/1976 | Toner | 378/168 |

FOREIGN PATENT DOCUMENTS

| 0592218 | 7/1925 | France | 378/168 |
|---|---|---|---|
| 0790332 | 2/1958 | United Kingdom | 378/169 |

OTHER PUBLICATIONS

"Dental X-Ray Films", RINN, May 1940.

Primary Examiner—Constantine Hannaher
Assistant Examiner—Don Wong
Attorney, Agent, or Firm—Ernest D. Buff

[57] ABSTRACT

A radiographic film packet is adapted to be placed in a patient's mouth for exposing a sheet of dental film to x-rays generated by an x-ray tube. The packet includes a light-proof and moisture resistant envelope having a first side and a second side defining a pocket for receiving the film sheet.

Disposed within the pocket are a sheet of lead and a sheet of film, the lead sheet being located adjacent the second side and the film sheet being located between the lead sheet and the first side. An indicator affixed to the first side expressly designates the edge of the film packet appointed to be uppermost in the mouth during radiographic exposure. A film marker is affixed to said film sheet along a periphery and proximate a corner thereof. The film marker has a constant orientation relative to the indicator, and identifies the orientation of the film sheet during exposure.

22 Claims, 10 Drawing Sheets

MARKERS FOR DENTAL X-RAY FILM AND PACKETS FOR SIMPLIFIED FILM MOUNTING

CROSS-REFERENCE TO RELATED APPLICATION.

This Application is a Continuation-in-Part of copending U.S. application Ser. No. 572,264, filed Aug. 27, 1990 now abandoned.

BACKGROUND OF THE INVENTION

1. Field of the Invention

The present invention relates to the field of dental radiography; and more particularly, to means for establishing a constant exposure orientation, and positively identifying viewing orientation of dental X-ray film and copies made thereof.

2. Description of the Prior Art

A dental radiograph is an X-ray image of one or more teeth and surrounding bone that is achieved by placing an X-ray film, enclosed in a light-proof package, into the mouth, on one side of the dental structure, while an X-ray tube is aimed at the film from the other side of the structure, generally from outside the face. After the film is developed, it is customarily mounted in a frame of cardboard or plastic for viewing and storage. The mounting of dental radiographs for viewing can be a complex process and has been likened to solving a jigsaw puzzle, requiring a working knowledge of dental anatomy and facial osteology. Since adjacent teeth, opposing teeth, and teeth in the opposite side of the mouth may all appear similar to one another and since the mounting is often performed by technical personnel of varying degrees of training and experience, errors inevitably occur. If an error is made and escapes detection, it can lead to treatment of the wrong tooth.

The film is conventionally provided with a "button" along one edge. This button consists of a depression created in one surface of the film and a corresponding raised bump in the opposite surface. The raised side normally corresponds to the side of the film that faced the X-ray tube during exposure. Because of its large size relative to the structures being imaged, this button can cause unacceptable distortion in the underlying X-ray image. It is therefore recommended in the literature, as in "Dental Radiology" by Wuehrmann et al., that the button be positioned toward the occlusal plane so as not to superimpose on important dental structures.

While the button is intended to identify the exposure side of the film, it has several disadvantages. First, the button measures approximately 2 mm in diameter and over 3 square millimeters in area, and its curved surface results in distortion of the underlying image. It is therefore positioned close to the edge of the film to prevent it from superimposing on important structures, and it is thus frequently not visible on the mounted film, being partially or completely covered by the mounting frame. The viewer of a mounted film cannot then readily determine whether the film has been properly mounted without removing the film from the frame. Second, when copies are made of the original radiograph, an increasingly common practice because of the rise in dental consultation and litigation, the button is not consistently visible on such copies. The dentist receiving such copies is deprived of the orientation information provided by the button on the original film and may need to repeat the radiographs if there is a question of incorrect mounting. The film manufacturer normally impresses letters or symbols along one edge of the film for manufacturer's identification, but these impressions, like the button, are normally hidden by the mounting frame and are not consistently visible on radiographic copies.

French patent 2,618,917 to Zabiolle discloses a method of engraving an inscription on a plate that is attached to a dental X-ray film during exposure to mark the film with the inscription. Canadian patent 1,249,745 to Tanaka discloses an information bearing sheet for X-ray film made of paper or plastic with identification numbers printed in ink containing lead. The need remains in the art for a method and means capable of modifying X-ray dental film to: (1) establish a constant exposure orientation; and (2) positively identify the viewing orientation of the film and copies made thereof.

SUMMARY OF THE INVENTION

The present invention provides means for: (1) establishing a constant exposure orientation; and (2) positively identifying a constant mounting orientation of dental X-ray film and copies made thereof. Such identification simplifies the task of film mounting, saving time and substantially reducing the likelihood of human error.

Generally stated, the invention provides a radiographic film packet adapted to be placed in a patient's mouth for exposing a sheet of dental film to X-rays generated by an X-ray tube, comprising: a light-proof and moisture resistant envelope having a first side and second side defining a pocket for receiving the film sheet; a sheet of lead disposed within the pocket adjacent the second side; a sheet of film disposed within the pocket between the lead sheet and the first side; an indicator affixed to the first side of the envelope, the indicator expressly designating the edge of the film packet appointed to be uppermost in the mouth during radiographic exposure; and a film marker affixed to the film sheet along the periphery and proximate a predetermined corner thereof and having a constant orientation thereon relative to the indicator, for identifying the orientation of the film sheet during exposure.

In use, the invention provides means for establishing a constant exposure orientation. The invention further provides means for positively identifying viewing orientation of dental X-ray film, even when the film being viewed is a copy. The means are user friendly and reduce both the skill level and time required to correctly expose and mount film, thereby reducing the likelihood of error. The orientation of the mounting is readily evident on the original film and on copies made thereof, reducing the need for repeat X-rays and decreasing the chance of erroneous dental treatments.

In addition, the invention provides an improved process for radiographic exposure of dental film within a film packet. The improvement comprises the steps of (a) designating with an indicator the edge of the film packet appointed to be uppermost in the patient's mouth during the exposure; and (b) marking the film at a location thereon having constant orientation relative to the indicator.

BRIEF DESCRIPTION OF THE DRAWINGS

The invention will be more fully understood and further advantages will become apparent when reference is made to the following detailed description of the preferred embodiment of the invention and the accompanying drawings, in which.

DESCRIPTION OF THE PREFERRED EMBODIMENTS

Figure 1:
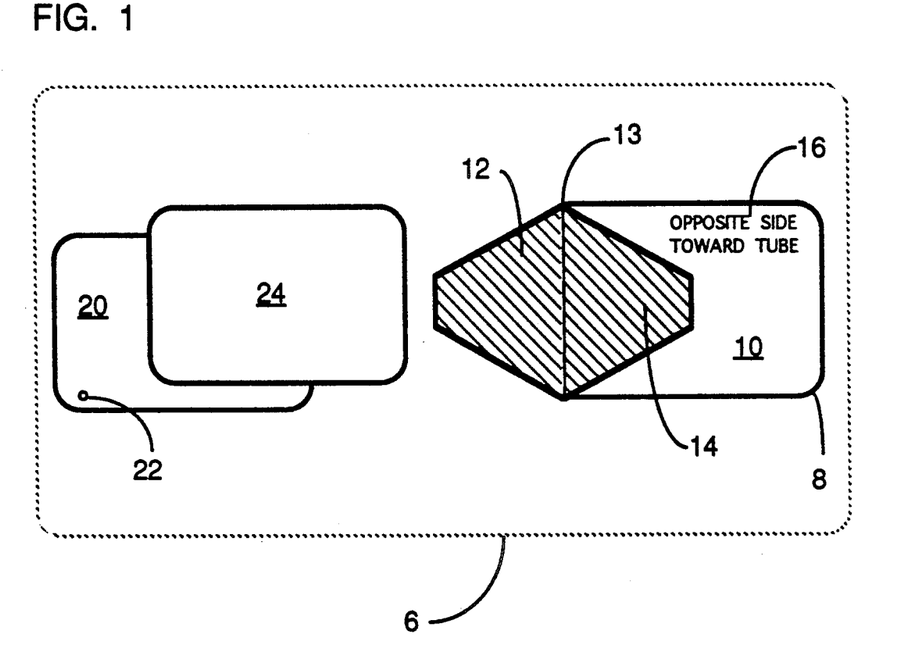
FIG. 1 is a schematic rear side view of the components of a radiographic dental film packet.
Figure 2:
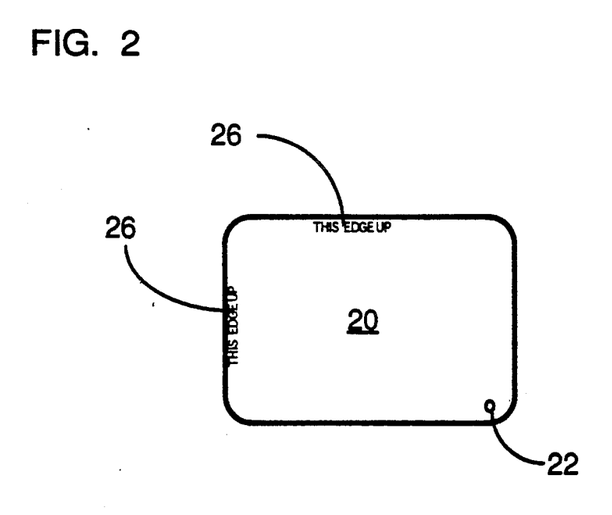
FIG. 2 is a schematic tube side view of a radiographic dental film sheet.

Referring to FIG. 1 of the drawings, radiographic dental film packet 6 comprises a light-proof and moisture resistant envelope 8 having a first side (shown at 28 in FIG. 3) and a second side 10 defining a pocket 14 to receive film sheet 20 and lead foil 24. Foil 24 is disposed between the film sheet 20 and second side 10 of envelope 8. Optionally, film sheet 20 is rapped with black paper to further protect the film sheet from light. Tab 12 folds at line 13 sealing envelope 8. Film sheet 20 is provided with film marker 22 along the periphery of film sheet 20 and proximate a corner. Preferably, film marker 22 comprises a perforation in film sheet 20, a notch on the edge of the film sheet 20, or a truncated corner, an area substantially free of emulsion, or a light-opaque material, such as ink, paint, decal, or pre-exposed film emulsion, whereby a copy of developed film sheet 20 will reliably reproduce an image of the marker 22. Alternatively, film marker 22 comprises a letter, word or symbol indicating the tube side of film sheet 20, whereby a copy of developed film sheet 20 will contain an image of film marker 22. As a further alternative, film marker 22 comprises an embossed or raised button along the edge of the film sheet 20. Preferably second side 10 of envelope 8 is provided with notice 16 indicating that the opposite side of the envelope 8 (or first side) is to face the X-ray tube during exposure. Optionally as shown in FIG. 2, film sheet 20 is provided with additional film marker 26, that specifically labels the upper edge of the film sheet viewing.

Figure 3:
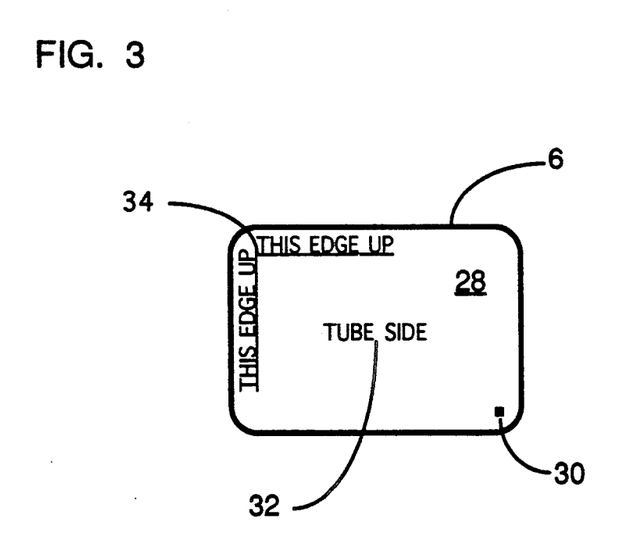
FIG. 3 is a schematic tube side view of a radiographic dental film packet.

Preferably, envelope 8 is rectangular in shape, giving the technologist the option of placing the film in the patient's mouth in either the vertical or horizontal orientation. Referring to FIG. 3 of the drawings, first (or tube) side 28 of envelope 8 is provided with first envelope indicator 34 designating the edge of the packet to be uppermost for vertical or horizontal exposures. Indicator 34 comprises a label, or symbol, thereby giving envelope 8 a visual means of identification. Alternatively, as shown in FIGS. 6A through 6D, indicator 34 comprises a roughened 51, scalloped 53, embossed 55, dented or raised 57 edge of the envelope 8, thereby giving envelope 8 tactile means of identification. Optionally, second envelope indicator 32 designates the side of the packet appointed to face the x-ray tube during exposure, and third indicator 30 designates the position of film marker 22 within envelope 8.

Figure 4:
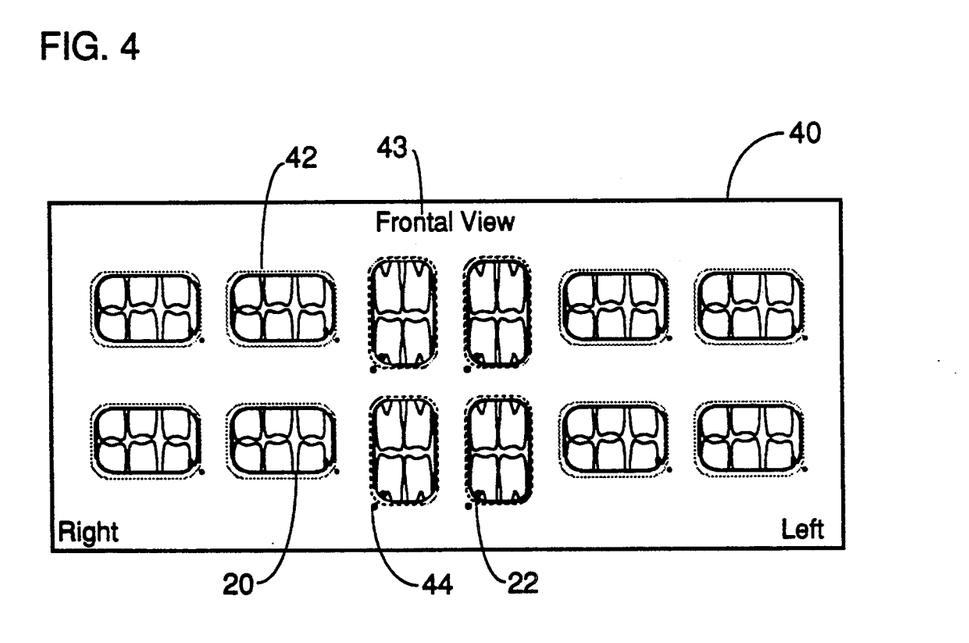
FIG. 4 is a schematic frontal view of developed dental films mounted in a viewing frame.
Figure 5:
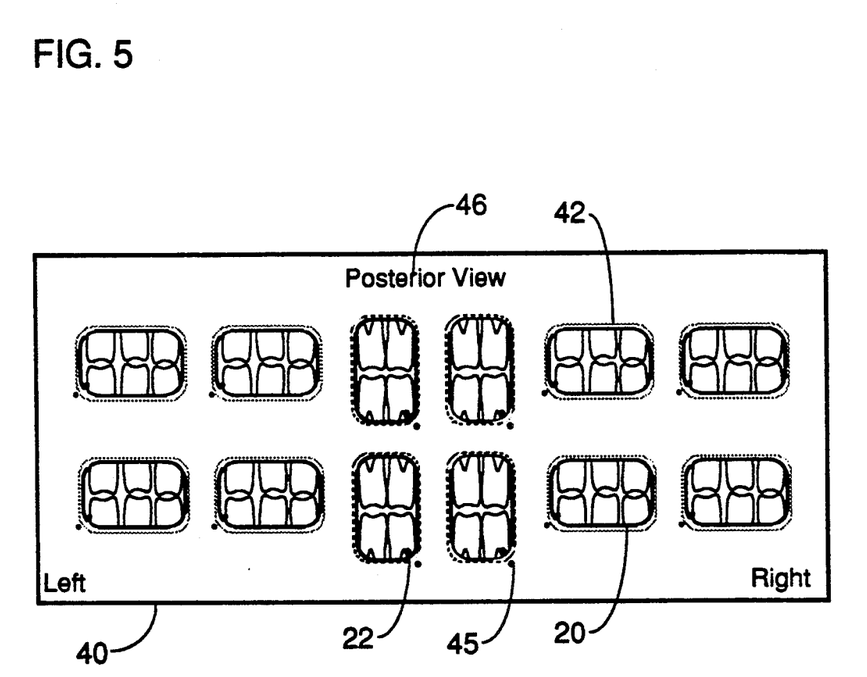
FIG. 5 is a schematic posterior view of developed dental films mounted in a viewing frame
Figure 6A:
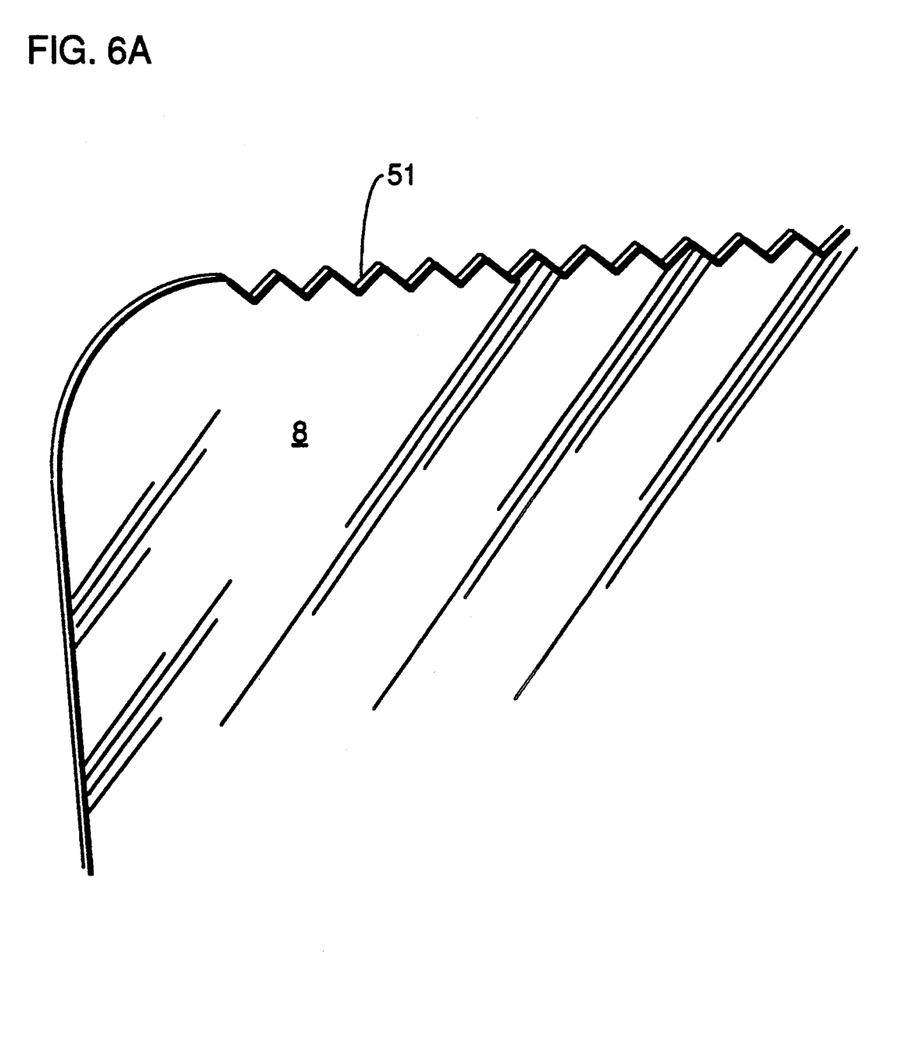
FIGS. 6A, 6B, 6C and 6D are perspective views of dental film packets wherein edges that are roughened, scalloped, embossed, and raised, respectively are used to identify film packet orientation by tactile means.
Figure 6B:
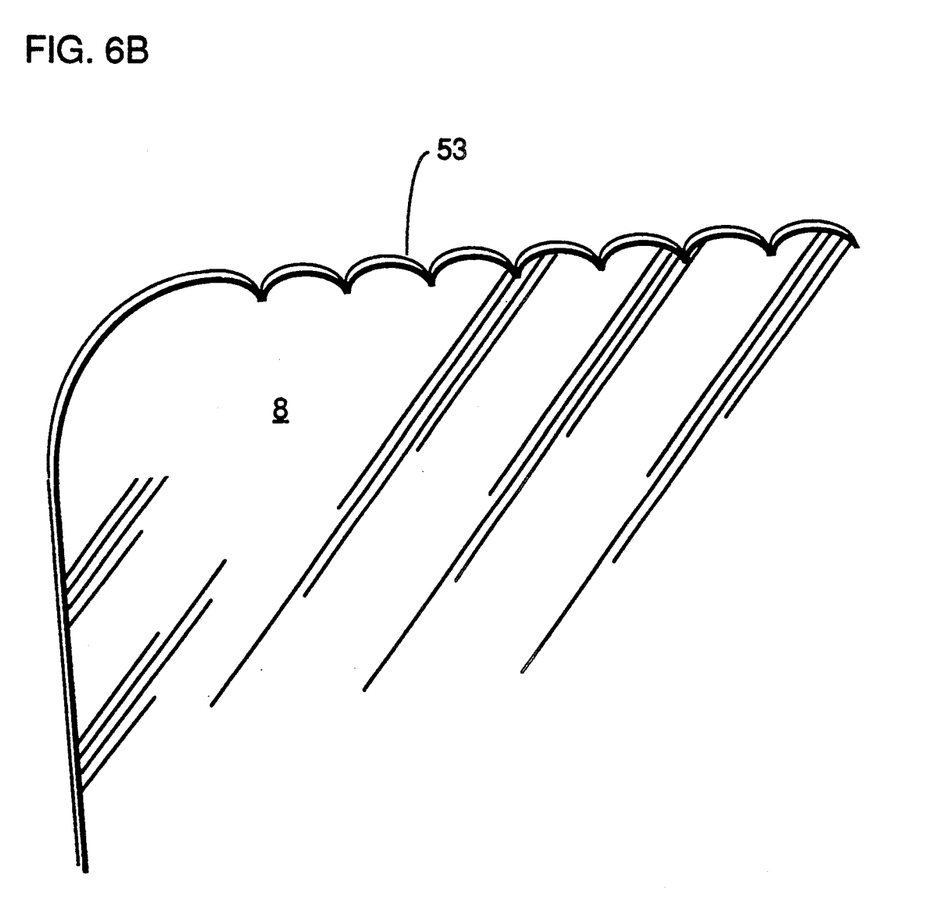
Figure 6C:
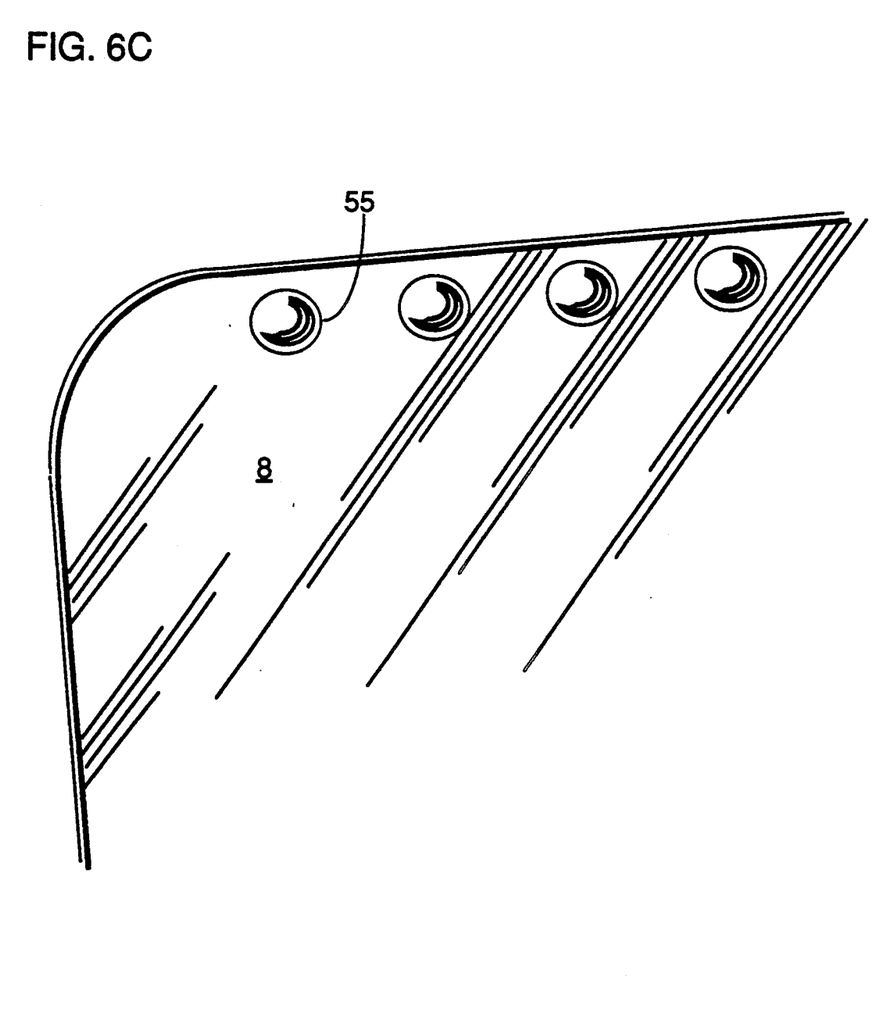
Figure 6D:
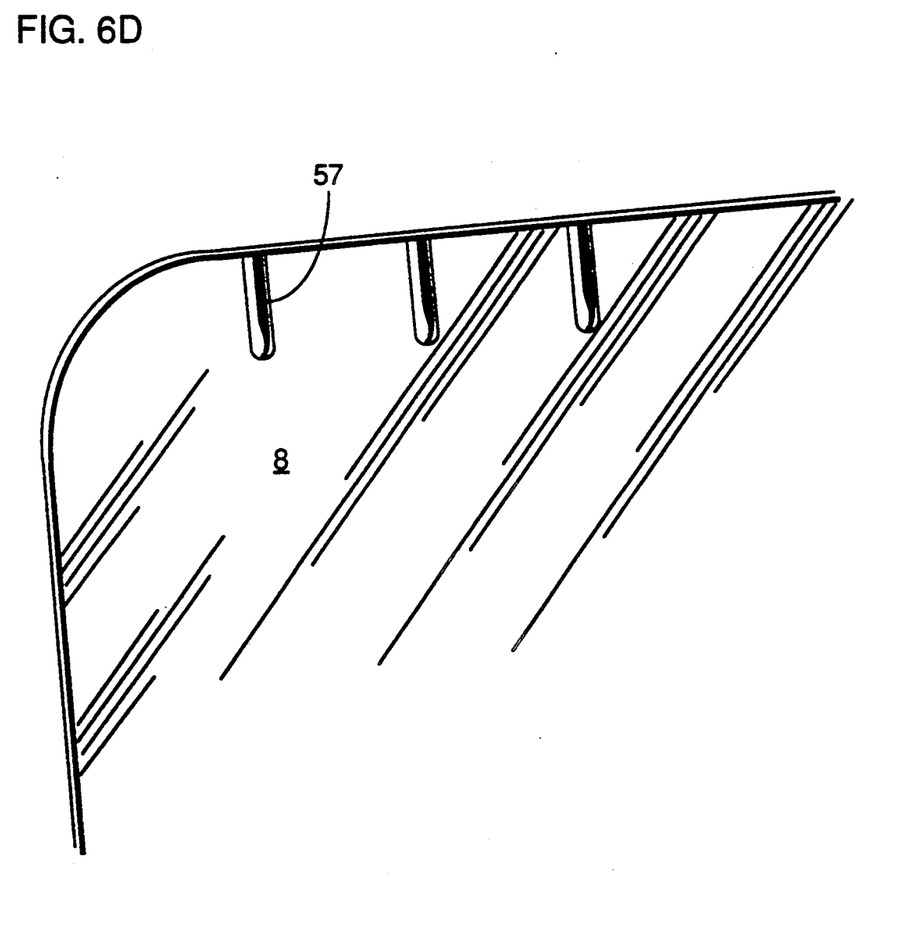
Figure 7:
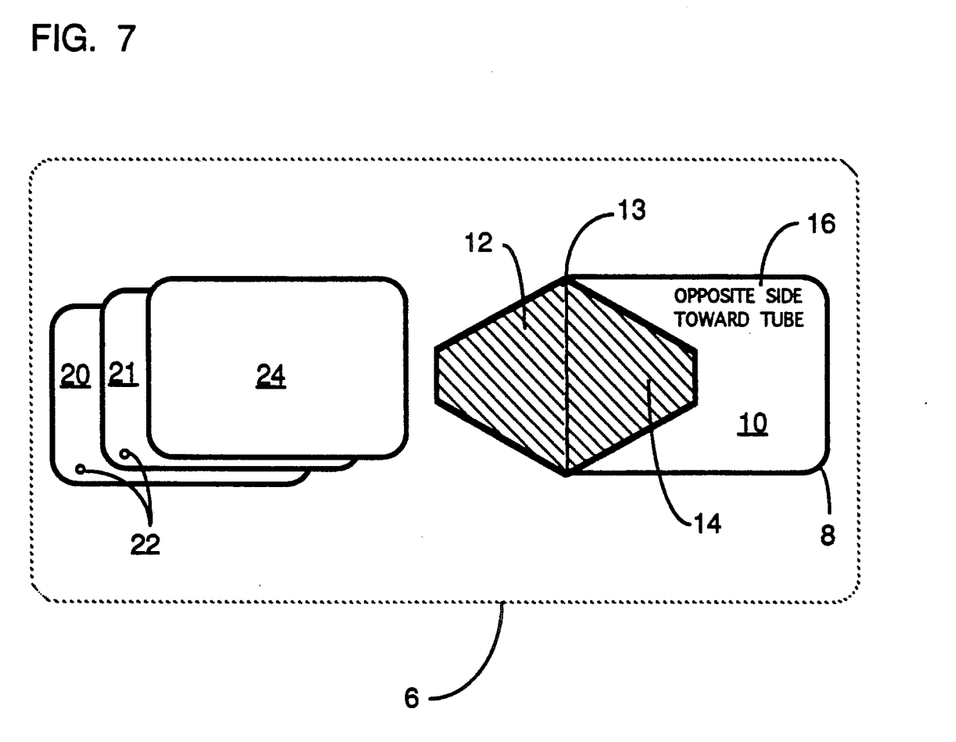
FIG. 7 is a schematic rear side view of the components of a radiographic dental film packet the contains a plurality of film sheets.

Preferably, as shown in FIG. 4, film marker 22 is positioned to appear within window 42 of viewing frame 40, so as to not be obscured when mounted therein. FIG. 4 displays the teeth as seen from the front of the patient. Preferably, film marker 22 is at least 1/16 inch from the edge of film sheet 20, thus allowing film marker 22 to be seen when mounted in frame 40. Preferably, viewing frame 40 is provided with labels 43 and 44 indicating the front of frame 40 and the standard location of marker 22 on mounting films. A rear or posterior view of viewing frame 40 is shown in FIG. 5. This view displays the teeth as seen from the back of the patient's mouth. FIG. 7 depicts a schematic rear side view of the components of a radiographic dental film packet containing a second film sheet 21.

In use, the dental technologist places film packet 6 in the patient's mouth with the tube side 28 facing the X-ray tube, and with one of the first envelope indicators 34 uppermost, depending on whether envelope 8 is oriented vertically or horizontally. After exposure all films are developed and mounted in viewing frame 40, each with film marker 22 oriented in a constant location, in one designated corner for horizontally oriented films and in a second designated corner for all vertically oriented films. Film marker 22 is readily visible and facilitates mounting films within viewing frame 40. When films are properly mounted and viewed from the exposure side, film marker 22 will be in the same corner as it was when the films were exposed, and are disposed in the corner of the frame nearest frame marker 44 (or frame marker 45 when viewed from the reverse side of frame 40).

As an example, an exposed set of 14 Kodak Safety dental films, which the manufacturer marks with both a button and the letters "KS" along an edge, were each modified with a perforation placed a minimum 1/16 inch from the film edge and of diameter varying from ½ millimeter to 1 mm. A Healthco EZ Mount cardboard frame was modified by marking the front lower right-hand corner of each horizontal window and the front lower left-hand corner of each vertical window with an ink dot. Each film was mounted, with the film perforation in a corner closest to the window dot, in the Healthco EZ Mount cardboard frame. Both the manufacturer's button and identifying letters were obscured by the frame, whereas the perforation was clearly visible on each of the film sheets. When copies were subsequently made of the set, the image of each perforation was clearly seen on all copies, whereas the image of the button was only visible on three of the fourteen and the "KS" was not visible on six of the fourteen.

The invention has been described in detail with particular reference to the preferred embodiments thereof, but it will be understood that additional variations and modifications may suggest themselves to one skilled in the art, all falling within the scope of the invention as defined by the subjoined claims.

What is claimed is:

1. A radiographic film packet adapted to be placed in a patient's mouth for exposing a sheet of dental film to X-rays generated by an X-ray tube, comprising:
   (a) a light-proof envelope having a first side and second side defining a pocket for receiving said film sheet;
   (b) a sheet of lead disposed within said pocket adjacent said second side;
   (c) a sheet of film disposed within said pocket between said lead sheet and said first side;
   (d) an indicator affixed to said first side of said envelope, said indicator expressly designating the edge of said film packet appointed to be uppermost in said mouth during radiographic exposure; and (e) a film marker affixed to said film sheet along the periphery and proximate a predetermined corner thereof, said marker being reliably reproducible on all copies of said film sheet and having a constant orientation thereon relative to said indicator, for identifying the orientation of said film sheet during exposure.

2. A radiographic film packet as recited in claim 1, having a second sheet of film adjacent to said first sheet of film.

3. A radiographic film packet as recited in claim 1, wherein said indicator is selected form the group consisting of roughened edges, scalloped margins, embossed, and raised lines, thereby identifying said edge by tactile means.

4. A radiographic film packet as recited in claim 1, wherein said indicator selected form a group consisting of printed lines, words, and symbols.

5. A radiographic film packet as recited in claim 1, further comprising a second indicator disposed on said first side of said envelope adjacent to said film sheet, for designating the exposure side of said radiographic film packet.

6. A radiographic film packet as recited in claim 5, further comprising a third indicator disposed on said first side of said envelope adjacent to said film sheet and in alignment with said film marker, for designating the location of said film marker inside said radiographic film packet.

7. A radiographic film packet as recited in claim 1, wherein said film marker comprises a perforation in said film sheet.

8. A radiographic film packet as recited in claim 7, wherein said perforation has a diameter ranging from about 1/4 to 1 millimeter.

9. A radiographic film packet as recited in claim 1, wherein said film marker comprises a notch located along the edge of said film sheet.

10. A radiographic film packet as recited in claim 1, wherein said film marker comprises an area of film sheet substantially free from emulsion.

11. A radiographic film packet as recited in claim 1, wherein said film marker comprises a truncated corner of said film sheet.

12. A radiographic film packet as recited in claim 1, wherein said film marker comprises a printed label, symbol or lettering that expressly indicates the side of said film sheet that faced said X-ray tube during exposure.

13. A radiographic film packet as recited in claim 1, wherein the center of said film marker is located at least 1/16 inch from an edge of said film sheet.

14. A radiographic film packet as recited in claim 1, wherein said film marker comprises a label indicating that either of two edges of said film is appointed to be lace uppermost during viewing.

15. A radiographic film packet as recited in claim 1, wherein said light-proof envelope is moisture resistant.

16. In a process for radiographic exposure of dental film within a film packet, the improvement comprising the steps of:

(a) designating with an indicator the edge of the film packet appointed to be uppermost in the patient's mouth during said exposure; and (b) marking the film at a location thereon having constant orientation relative to said indicator, said marking being reliably reproducible on all copies of said film.

17. A process as recited by claim 16, wherein said dental film comprises at least one sheet of film.

18. A process as recited by claim 17, wherein said dental film comprises a plurality of sheets of film.

19. A process as recited by claim 17, wherein said location is preselected and said orientation of said markers relative to said indicator identifies the orientation of said film sheet during exposure.

20. A process as recited by claim 19, wherein said location is along the periphery and proximate a predetermined corner of said film sheet.

21. A process as recited by claim 17, wherein said film packet comprises a light-proof and moisture resistant envelope having a first side and a second side defining a pocket for receiving said film sheet and a sheet of lead disposed within said packet adjacent said second side, and said process further comprises the step of disposing said film sheet within said pocket between said lead sheet and said first side.

22. A process as recited by claim 21, wherein said envelope further comprises a sheet of black paper and said process further comprises the steps of disposing said sheet of black paper within said packet adjacent said first side and said sheet of lead, the disposition being such that said sheet of black paper is wrapped around and envelopes said film sheet within said pocket.

* * * * *